United States Patent [19]

Sorenson et al.

[11] 4,006,745
[45] Feb. 8, 1977

[54] AUTOLOGOUS TRANSFUSION SYSTEM AND METHOD

[75] Inventors: James L. Sorenson; Karl A. Pannier, Jr., both of Salt Lake City; Gordon S. Reynolds, Bountiful, all of Utah

[73] Assignee: Sorenson Research Co., Inc., Salt Lake City, Utah

[22] Filed: Nov. 13, 1975

[21] Appl. No.: 631,584

Related U.S. Application Data

[63] Continuation-in-part of Ser. No. 580,087, May 22, 1975.

[52] U.S. Cl. .............................. 128/214 R; 128/276
[51] Int. Cl.² ..................... A61M 1/00; A61M 5/00
[58] Field of Search ....... 128/214 R, 214 A, 214 B, 128/214 C, 214 D, 214.2, 231, 232, 276, 278, DIG. 3; 137/205, 564.5; 222/95, 386.5

[56] References Cited

UNITED STATES PATENTS

| | | | |
|---|---|---|---|
| 3,021,841 | 2/1962 | Burke | 128/214 C |
| 3,191,600 | 6/1965 | Everett | 128/276 |
| 3,492,991 | 2/1970 | Dyer | 128/214 R |
| 3,701,433 | 10/1972 | Krakauer et al. | 128/214 C X |
| 3,742,952 | 7/1973 | Magers et al. | 128/230 X |
| 3,788,374 | 1/1974 | Saijo | 128/272 X |
| 3,866,608 | 2/1975 | Reynolds et al. | 128/276 |
| 3,896,733 | 7/1975 | Rosenberg | 128/214 R |
| 3,965,896 | 6/1976 | Swank | 128/214 R |

Primary Examiner—Edgar S. Burr
Assistant Examiner—Paul T. Sewell
Attorney, Agent, or Firm—H. Ross Workman; J. Winslow Young

[57] ABSTRACT

An autologous blood transfusion system comprising at least two interconnected blood receptacles, the first of which is evacuated and connected to a suction device for aspirating blood. The second receptacle takes blood from the first by overcoming the vacuum in the first with a greater vacuum in the second without interrupting the ability of the suction device to simultaneously aspirate blood. The second receptacle may comprise a transfer bag for reinfusion into the patient or an infusion set may be connected to the second receptacle to permit simultaneous collection of the blood from the patient and infusion of the blood back into the patient. In either case, the second receptacle is selectively exposed to positive pressure to expel the blood from the second receptacle into the transfer bag or patient. The method includes aspirating blood from the patient and collecting blood in the first receptacle. Blood is thereafter transferred to the second receptacle by increasing the vacuum in the second receptacle over the first receptacle without interrupting the ability of the suction device to simultaneously aspirate blood. Blood is then expelled from the second receptacle by subjecting the blood within the second receptacle to positive fluid pressure.

22 Claims, 8 Drawing Figures

AUTOLOGOUS TRANSFUSION SYSTEM AND METHOD

BACKGROUND

Related Application

This application is a continuation-in-part of copending U.S. patent application Ser. No. 580,087 filed May 22, 1975.

FIELD OF THE INVENTION

The invention relates to system and methods for autologous blood transfusion.

The Prior Art

Homologous blood transfusion is the well-known technique of collecting blood from a donor and thereafter storing the blood for later infusion into another patient. For many years, homologous blood transfusion has been the standard technique for replacing a patient's blood after surgery, obstetrical complications, traumatic hemorrhage and the like.

Homologous blood transfusion has evidenced a number of serious complications. For example, frequently elective surgical procedures must be postponed because of the unavailability of compatible homologous blood. In smaller towns and cities, there is frequently a lack of qualified donors. Also in larger metropolitan areas, there is a great need for quantities of blood to cover trauma situations and the increasing number of elective major surgical procedures. It is well-known that homologous blood must be cross matched to ascertain compatibility before the homologous blood is administered to a patient. Cross matching is an expensive and time consuming procedure and is not always effective in detecting blood incompatibility.

At present, the most serious complication due to homologous blood transfusion is post-transfusion hepatitis. The National Heart and Lung Institute has reported hundreds of deaths and thousands of cases of incapacitating illness resulting from post-transfusion hepatitis. Other complications, well-known in homologous blood transfusion, include isoimmunization, transmission of disease, incompatibility, hemolytic reactions and over transfusion.

These problems are substantially circumvented through the technique of autologous blood transfusion. Autologous transfusion is defined as the reinfusion of the patient's own blood. The desirability of autologous transfusion has been acknowledged for many years. Structure accommodating autologous transfusion is disclosed in applicant's U.S. Pat. No. 3,866,608 and in U.S. Pat. No. 3,896,733. Until this present invention, however, no structure and method has been known which would accommodate reinfusion of a patient's blood without interrupting the ability to simultaneously collect the blood. Further, until this present invention, no prior art is known which provides for rapid, essentially continuous collection of a patient's blood while reinfusing the blood back into the patient.

BRIEF SUMMARY AND OBJECTS OF THE INVENTION

The present invention comprises novel system and method for collecting a patient's blood in a first receptacle, and implementing variable fluid pressure for transferring the patient's blood to a second receptacle and thereafter reinfusing the patient without interrupting the collection process in the first receptacle.

It is, therefore, a primary object of the present invention to provide improvements in autologous blood transfusion.

It is another object of the present invention to provide a closed extracorporeal blood circuit defining a sterile blood path from collection to reinfusion.

One still further object of the present invention is to provide an autologous blood system and method accommodating continuous availability of suction at the blood aspiration site during collection and reinfusion of the blood.

One still further valuable object of the present invention is to provide structure and method accommodating reinfusion of blood simultaneous with collection of the blood.

Another important object of the invention is to provide structure and methods for transferring a patient's blood from a first to a second receptacle and back to the patient by alternating low and high fluid pressures in the second receptacle.

A further object of the present invention is to provide structure and method for interchanging second receptacles to accommodate the filling of several separate units from the first receptacle without requiring interruption of the blood collection process.

It is a further object of the present invention to provide structure and method for transferring blood from a first container to a second container by overcoming the vacuum pressure in the first container and thereafter emptying the second container without requiring interruption of the blood collection process.

These and other objects and features of the present invention will become more fully apparent from the following description and appended claims taken in conjunction with the accompanying drawing.

DETAILED DESCRIPTION OF THE PREFERRED EMBODIMENTS

The Apparatus

Figure 1:
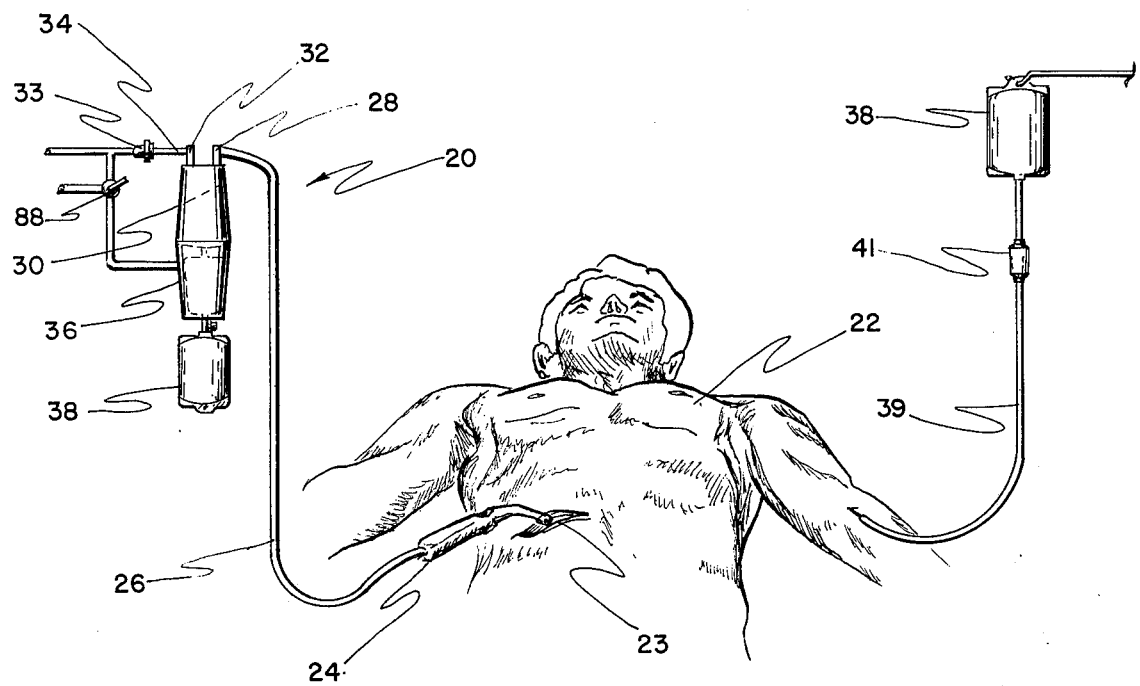
FIG. 1 is a schematic representation of one preferred embodiment of the invention illustrating structure and method for simultaneously collecting and infusing a patient's blood incorporating the embodiments of FIGS. 2–3 and 5–7.

Attention is now directed to the drawing wherein like numerals represent like parts throughout. Referring generally to FIG. 1, the autologous blood transfusion system generally designated 20 is schematically illustrated. The purpose for the autologous system 20 is to recover and reinfuse the blood of a patient 22. Normally, the source of blood from the patient will be through a wound or surgical incision represented at 23. Commonly, autologous blood transfusion has its greatest value under circumstances where great amounts of blood would normally be lost in a short period of time from the patient. A number of vascular, thoracic and abdominal surgeries could come within this category. Another significant area deals with hemorrhagic trauma resulting from injury to the patient. In either event, blood can normally be collected near the hemorrhage site.

It is presently preferred that the blood be collected with an aspiration wand 24 as is conventional. The aspiration wand 24 is connected by an elongated tube 26 to the inlet port 28 of a first receptacle 30. The first receptacle 30 has a vacuum port 32 conventionally connected to a vacuum line 34 which communicates with a conventional vacuum source (not shown) through a conventional pressure reducer 33.

The first receptacle 30 is evacuated through the vacuum line 34 so as to create a suction in the aspiration wand 24 and tube 26. Thus, blood is aspirated at the wand 24 and deposited in the first receptacle 30. It is presently preferred that the aspiration wand 24 be provided with the capability of mixing anticoagulant with the aspirated blood as disclosed in copending application Ser. No. 555,008 filed Mar. 3, 1975.

After the blood has been collected in the first receptacle, it must be communicated to a second receptacle 36. It is apparent by reference to FIG. 1 that without some force being exerted upon the blood, the blood will not move out of the first receptacle 30 into the second receptacle 36. Failure of the blood to naturally transfer into the second receptacle results because there is a significant negative pressure within the first receptacle, normally on the order of magnitude of 30 millimeters of mercury (mm Hg). Further, when the second receptacle is coupled directly to a flexible transfer bag 38, atmospheric pressure will discourage blood flow into the second receptacle 36. Structure must be provided, therefore, which will facilitate transfer of blood from the first receptacle 30 to the second receptacle 36.

Figure 2:
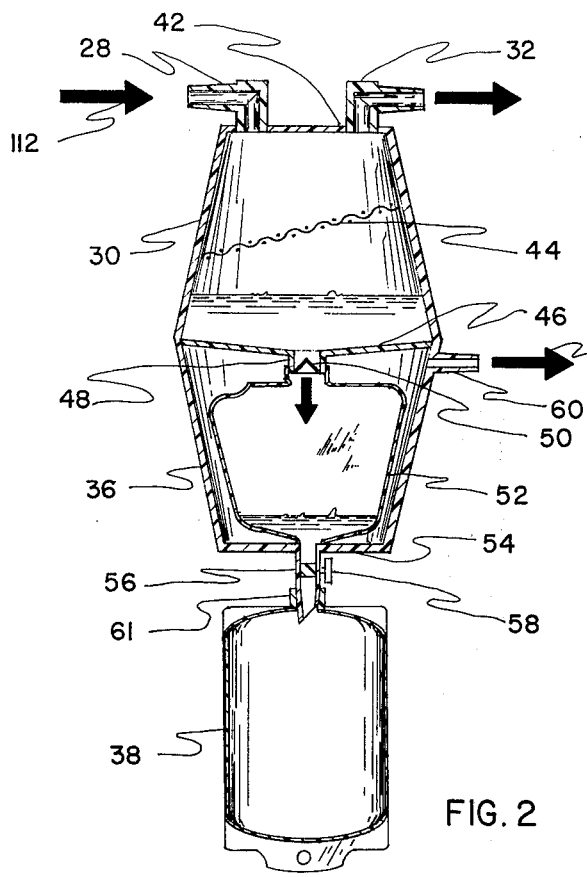
FIG. 2 is a schematic cross-sectional illustration of a presently preferred embodiment of a receptacle assembly forming part of the system of the invention as the second receptacle is being filled.

Referring now particularly to FIG. 2, the first receptacle 30 is illustrated as a rigid, transparent plastic container. The top or cap 42 of the container is provided with diametrally opposed ports 28 and 32. The port 32 is connected through the vacuum line 34 (see FIG. 1) to a vacuum source (not shown). The inlet port 28, as described above, is connected to the tube 26 (see FIG. 1). Blood passing through the tube 26 enters the interior of the first receptacle 30 at the port 28.

Filter screen 44 is placed in the blood receiving chamber or receptacle 30 so as to transect receptacle 30 and thereby serve as a filter screen for all blood entering receptacle 30. Filter screen 44 assists in removing entrained air in the blood and in separating out tissue fragments and the like aspirated with the blood. Preferentially, the plane of filter screen 44 is angularly oriented with respect to the axis of receptacle 30 so as to permit the screened fragments to collect at a low point and not clog the filter screen 44.

The first receptacle 30 has a bottom 46 which tapers conically downwardly and carries a depending boss 48. The boss 48 confines a unidirectional valve 50. Thus, blood collected in the receptacle 30 will pool at the bottom 46 toward the center thereof at the location of the valve 50.

Figure 5:
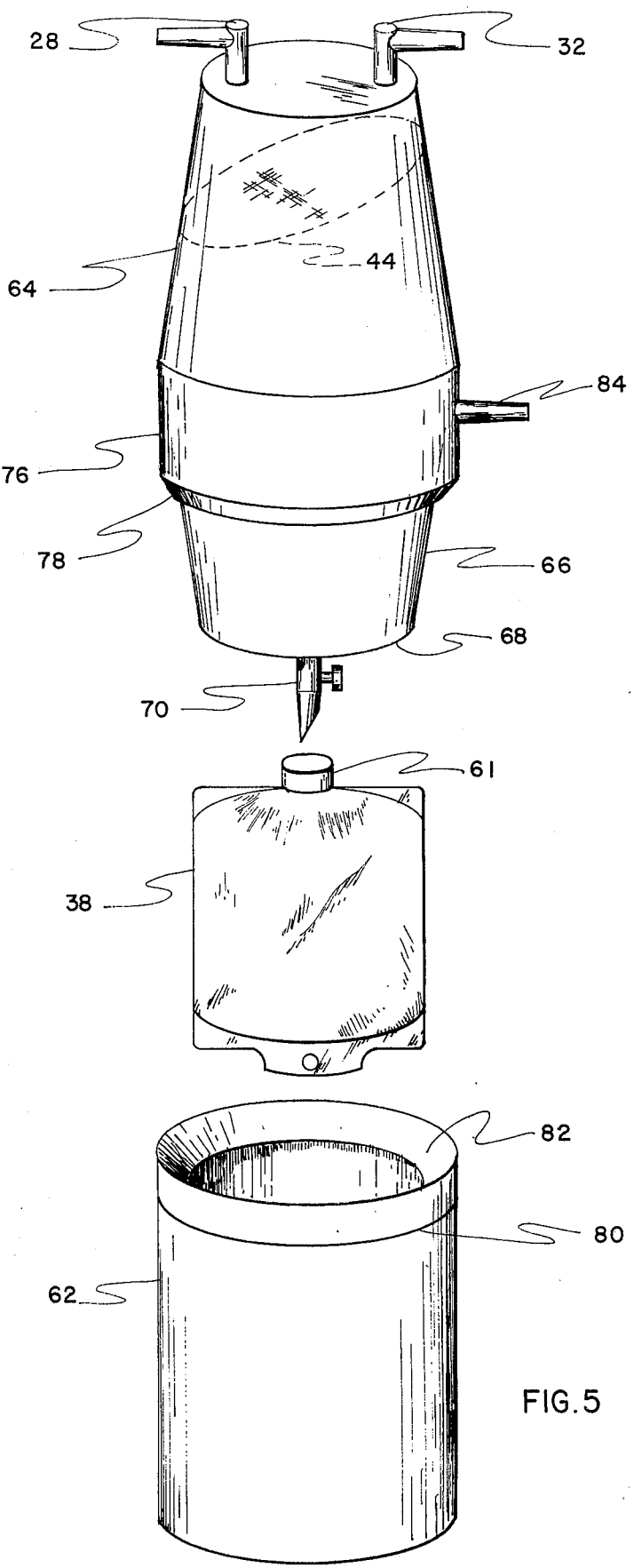
FIG. 5 is an exploded perspective illustration shown partly schematically of still another preferred embodiment of the invention.

The second receptacle 36 is located downstream from the receptacle 30 and may be unitary with the first receptacle 30, as shown in FIG. 2, or initially separate as shown in FIG. 5, hereinafter more fuly described. The second receptacle 36 in the embodiment of FIGS. 1 and 2 is a rigid plastic container which substantially circumscribes a flexible liner 52. The flexible liner 52 may be secured in any desirable way to the interior of the second receptacle 36, direct attachment to the boss 48 being illustrated in FIGS. 2 and 3. It should be noted that the liner is attached to the boss 48 such that the interior of the first receptacle 30 communicates with the interior of the liner 52 through the valve 50. Initially, flexible liner 52 is completely collapsed prior to the introduction of blood therein so as to minimize air/blood contact.

A depending spike 56, preferably having a valve 58 therein, is mounted upon the bottom 54 of receptacle 36. The hollow liner 52 opens into the spike 56 so that the contents of the liner 52 can be expelled through the spike 56 as will be subsequently more fully described. The valve 58 may be automatic or manual, the manual variety being shown in FIGS. 2-4 for simplicity.

The second receptacle 36 is provided with at least one fluid pressure port 60 which communicates with the interior of the receptacle 36 between the receptacle 36 and the liner 52. The second receptacle 36 may be evacuated through the fluid pressure port 60 as shown in FIG. 2 or, alternatively, a positive pressure may be exerted between the liner 52 and the receptacle 36 through the port 60 as shown in FIG. 3.

The flow of blood between receptacle 30 and liner 52 is controlled in part by check valve 50 mounted between the first and second receptacles, the check valve 50 being of conventional well-known construction. An example of a suitable check valve is found in U.S. Pat. No. 3,742,952. The check valve is constructed to limit the flow of blood unidirectionally from the first receptacle 30 to the liner 52 within second receptacle 36 and to prevent retrograde flow. The valve 58 while illustrated as manually operable could also be similar to that of valve 50.

The second receptacle 36 may be connected to a blood storage container 38 as shown in FIG. 2. The container 38 may be a plastic blood transfer bag or other suitable container for maintaining and storing blood. In this FIG. 2 embodiment, the second receptacle 36 and liner 52 cooperate to (a) overcome the negative pressure in receptacle 30 so as to transfer the blood into liner 52 without interrupting the negative pressure in receptacle 30 and (b) transfer the blood in liner 52 to the transfer bag 38 while continuing to collect blood in the first receptacle 30. The transfer bag 38 is filled by collapsing the liner 52 so as to expel blood unidirectionally from the second receptacle 36 into the transfer bag 38. The transfer bag 38 is removably attached to the spike 56 at the puncture site 61 of bag 38 so that the blood in transfer bag 38 can be reinfused into the patient as shown in FIG. 1. If desired, the puncture site 61 may be of self-sealing material. Notably, detachment of the transfer bag 38 from the second receptacle 36 will not seriously interfere with the collection of blood in the first receptacle 30.

Figure 3:
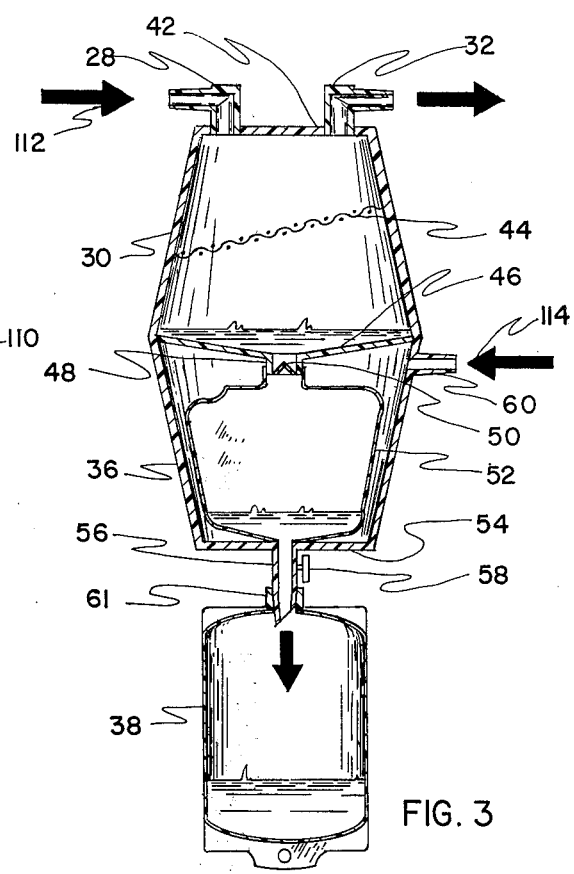
FIG. 3 is a schematic cross-sectional view of the embodiment of FIG. 2 as the second receptacle is being emptied.

In the operation of the embodiment of FIGS. 2 and 3, the valve 88 (FIG. 1) is situated so as to evacuate (as represented by arrow 110, FIG. 2) the space between the liner 52 and the receptacle 36. This reduced pressure expands liner 52 and unidirectionally transfers blood from receptacle 30 through the valve 50 into the liner 52. Thereafter, valve 58 is opened and valve 88 switched to pressure as represented by arrow 114 (FIG. 3). The elevated pressure source may be conventional pressurized gas available in most operating and emergency rooms. A conventional hand operated squeeze bulb could also be used to selectively develop elevated pressure at the port 60. Positive pressure thus created will develop between the liner 52 and the second receptacle 36 to force blood from liner 52 into the transfer bag 38. Retrograde flow from liner 52 into the first receptacle 30 is prevented by the one-way valve 50.

Clearly, successive collapse and recovery of the liner 52 in second receptacle caused by alternately decreasing and increasing fluid pressure between the liner 52 and receptacle 36 will deliver blood to a transfer bag 38 and, ultimately, to the patient without interfering with the ability to collect blood in receptacle 30 through wand 24 (FIG. 1).

Figure 4:
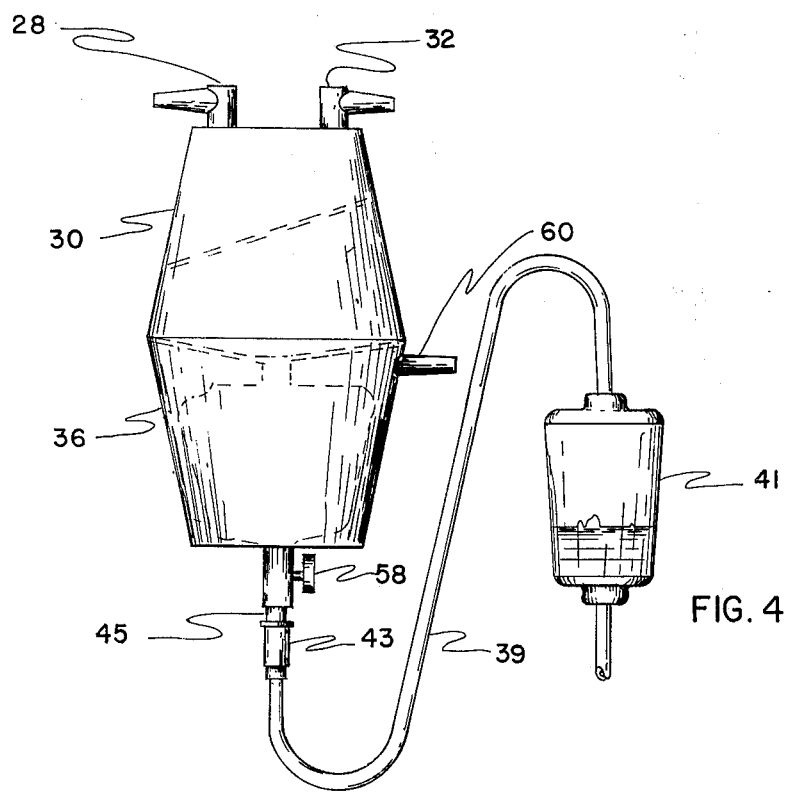
FIG. 4 illustrates an alternative receptacle embodiment usable to deliver blood directly to a patient.
Figure 8:
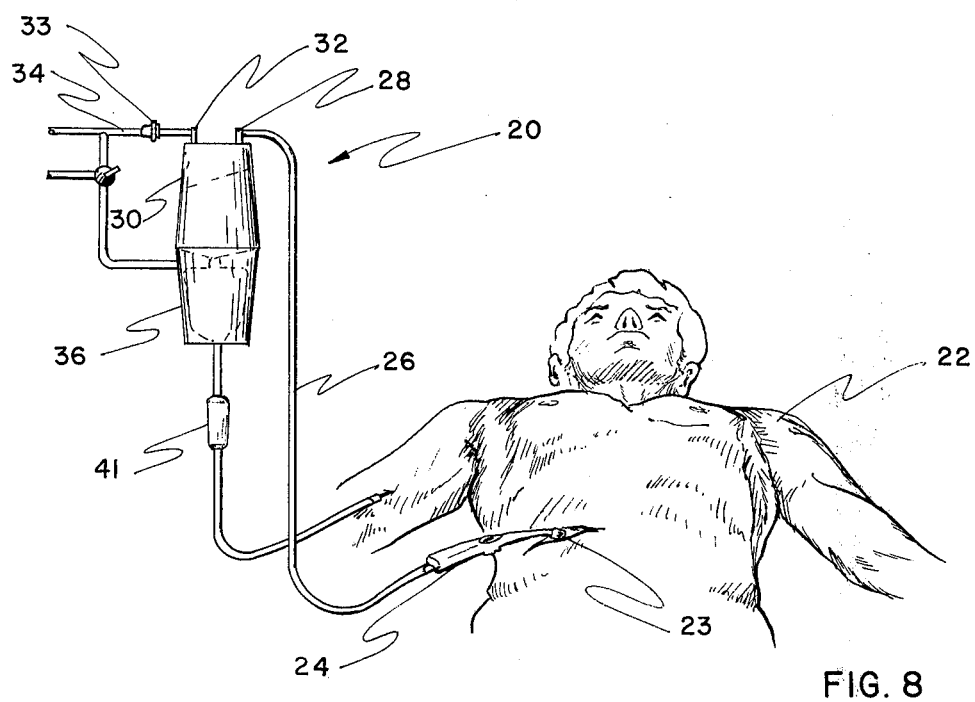
FIG. 8 is a schematic representation of the use of the embodiment of FIG. 4 illustrating structure and method for simultaneously collecting and infusing a patient's blood.

Alternatively, the second receptacle 36 may be connected directly to an infusion set 39 as shown in FIGS. 4 and 8. A conventional infusion set generally includes a drip chamber 41 and a female Luer fitting 43 adapted to mate within the coupling 45. Selectively, chamber 41 will include a fine mesh filter to act as a final filter for the blood prior to its reintroduction into the patient. This final filter in chamber 41 will be finer than filter screen 44 in order to remove any additional tissue fragments or other debris which could prove detrimental to the patient. The infusion embodiment of FIGS. 4 and 8 is preferred when it is desired to infuse blood into the patient immediately upon collection of the blood. The operation of the FIG. 4 and 8 embodiment is substantially the same as that described in connection with FIGS. 2 and 3 except that the collected blood is transferred directly to patient 22 rather than transfer bag 38.

Figure 6:
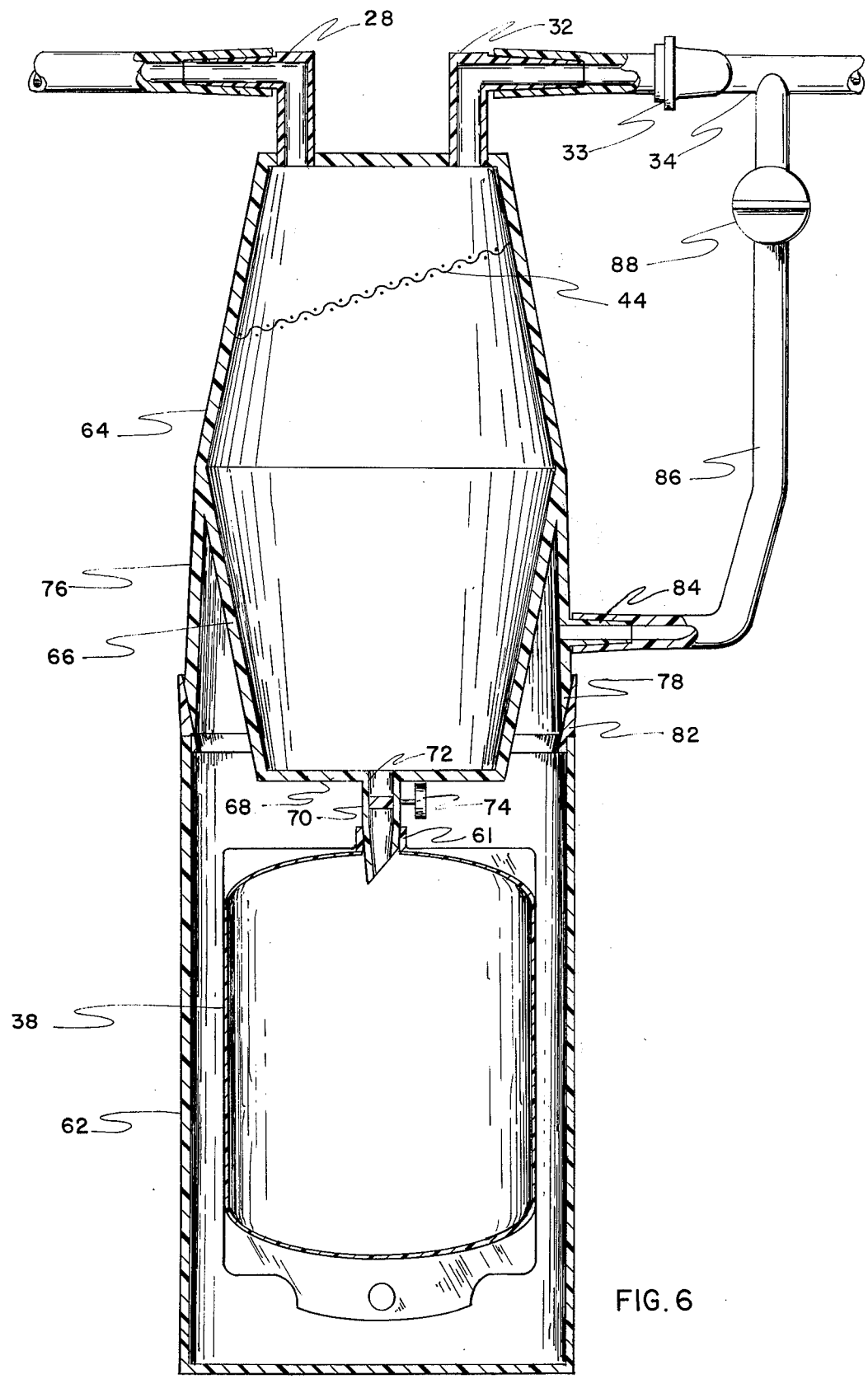
FIG. 6 is a cross-sectional view of the embodiment of FIG. 5 in the assembled form.

Another preferred embodiment of the present invention is illustrated in FIGS. 5 and 6. In FIGS. 5 and 6, the second receptacle embodiment designated 62 is detachable from the first receptacle 64. The first receptacle 64 includes a filter screen 44 and is similar to receptacle 30 except that the lower portion 66 thereof tapers inwardly conically and terminates in an essentially flat surface 68. A depending spike 70 is mounted upon the surface 68 and is hollow so as to communicate through opening 72 (see FIG. 6) with the interior of the receptacle 64. The spike 70 is preferably provided with a valve 74 which may be manual as illustrated or automatic and which selectively limits the flow of blood out of the receptacle 64. A transfer bag 38 having a puncture site 61 receives the spike 70 so as to be in open communication with the receptacle 64.

Receptacle 64 has an essentially cylindrical depending skirt 76, the lower edge 78 of the skirt being chamfered inwardly.

The second receptacle 62 is illustrated in essentially cylindrical configuration and has an open face 80 which is configurated to mate with the skirt 76 carried by the first receptacle 64. A sealing rim 82, formed of latex rubber or the like cooperates with the chamfered edge 78 to form a pressure seal at the interface of the skirt 76 and the receptacle 62. Thus, when the transfer bag 38 is secured to the spike 70, both the transfer bag and the bottom 66 of the receptacle 64 can be nested within the receptacle 62.

The skirt 76 presents at least one fluid pressure port 84 having a function substantially identical to that of fluid pressure port 60 described in connection with FIG. 2. When the transfer bag 38 and lower portion 66 of receptacle 64 are nested within the receptacle 62, the transfer bag 38 may be filled by evacuating receptacle 62 with a vacuum greater in magnitude than the vacuum in receptacle 64 thereby overcoming the negative pressure in receptacle 64 without interrupting the blood collecting process. After the transfer bag 38 has been filled, it may be easily removed by separating the receptacle 62 from the skirt 76 and disengaging the transfer bag 38. Thereafter, another, essentially identical transfer bag 38 may be substituted. It should be appreciated that suitable securing structure such as clips 122 (FIG. 7) may be used to restrain the receptacle 62 on the skirt 76.

The operation of the embodiment of FIG. 5 can best be understood by reference to FIG. 6. In FIG. 6, the first and second receptacles are illustrated in the assembled condition with the flexible bag 38 secured upon spike 70. In the assembly process, after the initially collapsed bag 38 has been attached to the spike 70, the valve 74 is opened to facilitate communication directly between the first receptacle 64 and the transfer bag 38. If valve 74 is an automatically operating unidirectional valve, e.g. valve 50 (FIG. 2), manual control of valve 74 is unnecessary.

Vacuum line 86 is connected through a three-way valve 88 to a source of vacuum in line 34 upstream from the pressure reducer 33. During assembly, the valve 88 is switched to off, it being observed that valve 88 does not interfere with vacuum through the port 32 so that blood may be continuously received at the port 28. As blood accumulates in the receptacle 64, the bag 38 and second receptacle 62 are assembled as shown in FIG. 6 and the valve 88 switched to vacuum. Because the vacuum in line 86 is upstream from the reducer 33, the vacuum in line 86 is greater than the vacuum imposed through the port 32. Accordingly, blood within the first receptacle 64 will be transferred through the spike 70 to the transfer bag 38.

After filling, the valve 88 is switched to vent and the valve 74 closed either manually or automatically as a result of increased pressure in receptacle 62. The transfer bag 38 is then removed and substituted by another. It is pointed out that the bag 38 in the FIGS. 5 and 6 embodiment closely resembles the operation of the liner 52 in the FIG. 2 embodiment.

While the embodiment illustrated in FIGS. 5 and 6 teach removal of the second receptacle 62 in order to access the transfer bag 38, other desirable ways of accessing the transfer bag 38 will be apparent to persons of ordinary skill in this art. For example, the receptacle 62 may be rigidly attached to the receptacle 64 and access to the bag 38 made through a door in the side or bottom of the receptacle 62.

Figure 7:
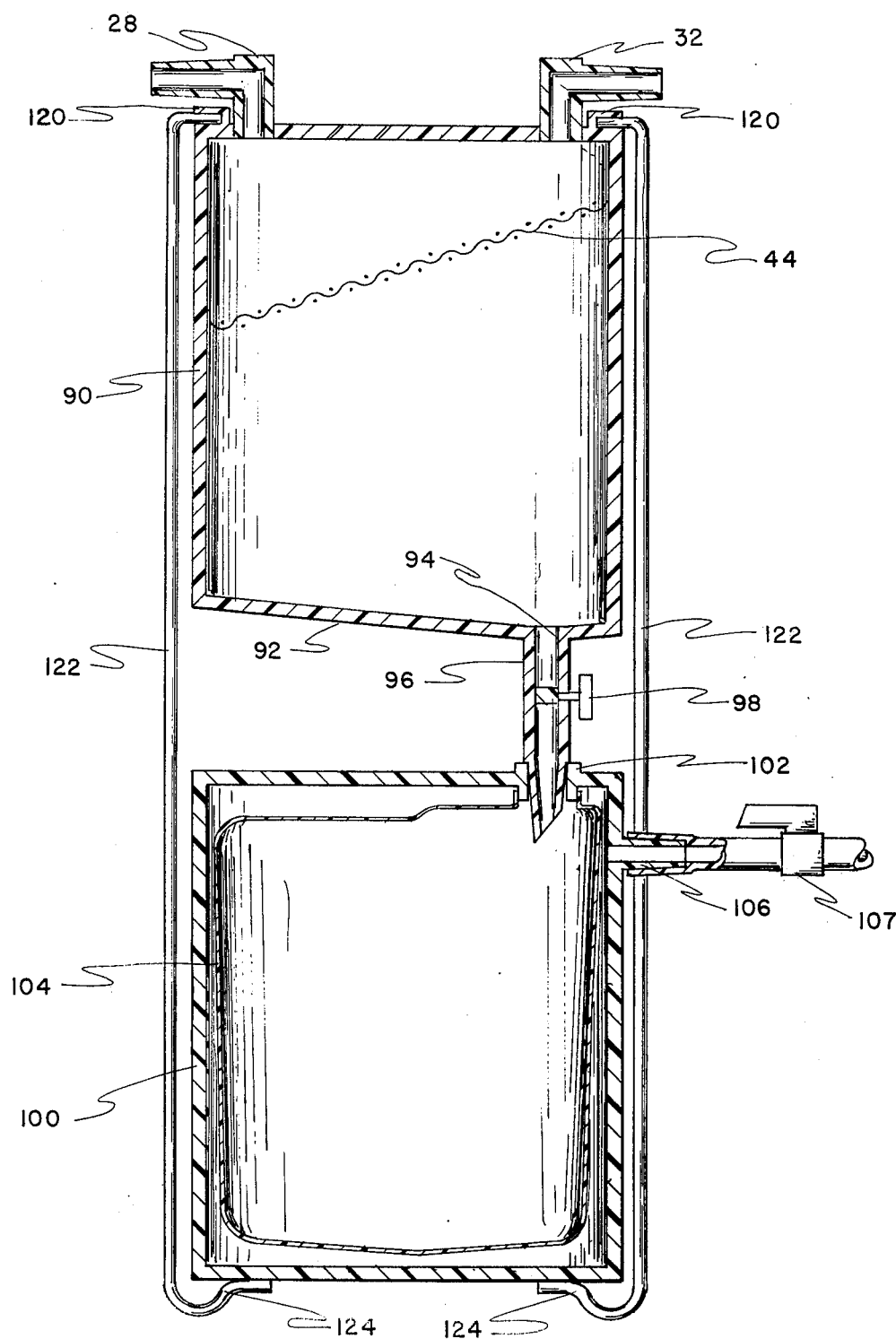
FIG. 7 is a schematic cross-sectional view of still another presently preferred embodiment of the invention.

FIG. 7 illustrates still another preferred embodiment of the invention comprising a first receptacle 90 having a blood inlet port 28 and a vacuum port 32 in the top thereof. As in the other embodiments, a suitable filter screen 44 may be implemented to strain tissue fragments and the like from the blood as set forth hereinbefore. The bottom 92 of the receptacle 90 is sloped to an orifice 94 which communicates with the hollow of a spike 96. The valve 98 and the spike 96 control the flow of blood out of the first receptacle. Valve 98 may be manual or automatic as hereinabove described. A second receptacle 100 has a coupling site 102 of self-sealing material which is penetrable by the spike 96. Interiorly, the receptacle 100 confines a flexible liner 104 which is secured at the coupling site 102 so as to admit blood passing through the spike 96 directly to the interior of the liner 104. At least one fluid pressure port 106 is formed in the wall of the receptacle 100. A valve 107 selectively evacuates or pressurizes the space between the liner 104 and receptacle 100.

In the operation of the embodiment of FIG. 7, the pressure between the liner 104 and the receptacle 100 is reduced by imposing a vacuum at the port 106. As long as the valve 98 is open and provided that the vacuum imposed through the port 106 is greater than the vacuum imposed through the port 32, blood in the first receptacle 90 will be transferred through the spike 96 to the interior of liner 104 within the receptacle 100. At any desirable time, the valve 98 may be closed and receptacle 100 removed from the spike 96 so as to provide a source of transfusion blood for patient 22 (see FIG. 1).

For ease of illustration, receptacle 100 is supported on spike 96 by spring clips 122 each of which is embedded at one end in a securement 120 in receptacle 90 and presents a biased support end 124. Support end 124 urges the receptacle 100 toward spike 98. Clips may be removed by urging the biased support ends outwardly against the resilience of spring clip 122 to permit the downward removal of receptacle 100 from spike 96. Alternatively, spring clip 122 may be rotatably engaged at securement 120 so as to permit rotation of spring clip 122 about securement 120 and thereby move support end 124 away from the bottom of receptacle 100.

After removal of the receptacle 100, a conventional infusion set (e.g. reference 39 in FIG. 1) may be attached to the coupling site 102. By exerting positive pressure through the port 106, the blood may be forcibly expelled from the liner 104 into the patient. Additionally, another substantially identical receptacle 100 may be secured to the receptacle 90 at the spike 96 for additional collection. It should be observed that the filling of the liner 104 and exchange of receptacles 100 takes place without interrupting the blood collection process in the first receptacle 90.

The Method

The method of the present invention may be practiced in two related ways as represented by FIGS. 1 and 8. In both embodiments, the blood aspirated from the patient 22 is conducted through a sterile, closed extracorporeal blood circuit.

Referring particularly to FIGS. 2 and 3, the transfer bag 38 is connected to the receptacle 36. The valve 88 (FIG. 1) is situated so as to evacuate the space between the liner 52 and the receptacle 36 as represented (in FIG. 2) by arrow 110. This reduced fluid pressure expands the liner 52. As the liner 52 is expanded, blood will be unidirectionally transferred from receptacle 30 through the valve 50 into the liner 52. Selectively, the valve 58 is opened and valve 88 switched to pressure as represented by arrow 114 in FIG. 3. The positive fluid pressure between the liner 52 and the second receptacle 36 will then cause blood in the second receptacle 30 to flow into the transfer bag 38. Valve 50 prevents retrograde flow into the first receptacle.

Clearly, successive collapse and recovery of the liner 52 in second receptacle caused by alternately decreasing and increasing fluid pressure between the liner 52 and receptacle 36 will deliver blood to the patient without interfering with the ability of the wand 24 and receptacle 30 to collect blood. The extracorporeal blood system is sterile and over transfusion is significantly reduced inasmuch as the only blood conducted back to the patient is that which was taken out. Hemodilution resulting from contributions of anticoagulant and the like is minimal.

In FIG. 1, the transfer bag 38 (or 104 if the embodiment of FIG. 7 is used) is separated from its corresponding receptacle prior to infusing the blood back into the patient 22. It is of significance that the blood is transferred into the second receptacle without interrupting the suction at the wand 24. After the second receptacle has been filled from receptacle 30, it may be removed and another second receptacle attached to the first receptacle 30 without interrupting blood collection. The second receptacle may then be used to reinfuse the blood into the patient 22 either by gravity or by positive fluid pressure simultaneously with blood collection at the wand 24.

In the embodiment of FIGS. 4 and 8, the blood is aspirated at the wand 24, conducted through the tube 26 and deposited in the first receptacle 30 as represented by arrow 112 in FIG. 2. Prior to actual infusion of the blood into the patient, air may be expelled from the blood delivery system either with isotonic saline, blood or other suitable injectable solution. The flexible liner 52 is filled as the second receptacle 36 is evacuated as represented by arrow 110 (FIG. 2) and emptied when the second receptacle 36 is pressurized as represented by arrow 114 (FIG. 3). In accordance with the method of FIG. 8, however, the blood expelled from the liner 52 is delivered directly to the patient 22.

Sterile collection and reinfusion of autologous blood in accordance with the described methods is highly advantageous. Because the system is closed, extraneous contamination is minimized without undue effort. Placing a filter for microorganisms in the vacuum line 34 prevents contamination of the first receptacle 30 by the external vacuum source. Accordingly only the air aspirated with blood at the patient site 23 is permitted to mingle with collected blood. This aspirated air is derived from the sterile surgical field, or at least contains no more contamination than the patient is already exposed to at the site 23. Customary aseptic care in use of the infusion set 39 will maintain the blood circuit in a sterile condition. Thus, according to the present invention, autologous blood can be collected and infused without exposing the blood to the ambient.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An autologous transfusion system comprising in combination:

means for aspirating blood from a patient;

a first blood-receiving receptacle comprising means connected to the aspirating means for conducting blood from a patient to the interior of the first receptacle, means for imposing a negative pressure within the first receptacle of sufficient magnitude to accommodate aspiration of blood through the aspirating means;

a second blood-receiving receptacle connected to the first receptacle by a hollow conduit which communicates the interior of the second receptacle with the interior of the first receptacle, said second receptacle also comprising means for unidirectionally controlling blood flow from the first to the second receptacle;

means for conducting a pressurizing fluid selectively into and out of the second receptacle;

means for reducing the pressure exerted by the pressurizing fluid in the second receptacle below the pressure in the first receptacle so as to transfer blood from the first to the second receptacle;

means for removably attaching a blood transfer bag to the second receptacle so that blood communication from the second receptacle to the blood transfer bag is accommodated; and means for delivering the pressurizing fluid under positive pressure to the second receptacle of sufficient magnitude in relation to the pressure maintained in the first receptacle to expel the blood from the second receptacle into the blood transfer bag without interrupting the negative pressure in the first receptacle.

2. An autologous transfusion system as defined in claim 1 wherein said second receptacle further comprises a fluid inlet and outlet port in an exterior housing and means for varying the fluid pressure communicated through the inlet and outlet port, the fluid pressure selectively acting upon the second receptacle to move blood alternately (a) into the second receptacle from the first receptacle and (b) into the transfer bag from the second receptacle.

3. An autologous transfusion system comprising in combination:

means for aspirating blood from a patient;

a first blood-receiving receptacle comprising means connected to the aspirating means for conducting blood from a patient to the interior of the first receptacle, means for imposing a negative pressure within the first receptacle of sufficient magnitude to accommodate aspiration of blood through the aspirating means;

a second blood-receiving receptacle connected to the first receptacle by a hollow conduit which communicates the interior of the second receptacle with the interior of the first receptacle;

means for removably attaching an infusion set to the second receptacle so that a closed pathway from the interior of the second receptacle to a patient through the infusion set is formed; and means for alternately decreasing and increasing pressure applied by pressurizing fluid in the second receptacle with respect to the negative pressure maintained in the first receptacle, thereby alternately (a) transferring blood from the first receptacle to the second when the fluid pressure in the second receptacle is lower than the pressure in the first receptacle and (b) transferring blood from the second receptacle to the patient through the infusion set when the pressure in the second receptacle is higher than the pressure in the first receptacle.

4. An autologous blood transfusion system comprising in combination:

a first rigid blood-receiving receptacle comprising means for receiving blood from a patient and means for imposing a negative pressure within the first receptacle to thereby urge blood from the receiving means to the first receptacle;

a second rigid receptacle, a flexible liner normally mounted within the second receptacle and means accommodating unidirectional blood flow from the first receptacle to the interior of the liner, the liner further comprising a blood outlet means through which blood within the liner may be expelled; and means for alternately communicating high and low fluid pressures between the flexible liner and the second rigid receptacle, said alternating pressures being sufficiently high and low in comparison to the negative pressure maintained in the first receptacle to control the flow of blood into the liner from the first receptacle and out of the liner through the expelling means.

5. An autologous blood transfusion system as defined in claim 4 wherein said communicating means comprises at least one fluid port in the wall of the second receptacle and means for alternately evacuating the second receptacle and pressurizing the second receptacle with respect to the negative pressure maintained in the first receptacle.

6. An autologous blood transfusion system as defined in claim 4 further comprising a blood transfer bag removably attached to the expelling means and comprising means for delivering blood from the liner in the second receptacle to the transfer bag in response to positive fluid pressure between the liner and the second receptacle.

7. An autologous blood transfusion system comprising in combination:

a first rigid blood-receiving receptacle comprising means for receiving blood from a patient and means for imposing a negative pressure within the first receptacle to thereby urge blood from the receiving means into the first receptacle;

a blood transfer bag removably attached to the first receptacle and blood outlet means for communicating the blood from the first receptacle to the transfer bag;

a canister into which the blood transfer bag and first receptacle are received to form a pressure seal between the canister and the first receptacle and comprising means for selectively accessing the blood transfer bag; and means for reducing the fluid pressure exerted upon the blood transfer bag within the canister below the level of negative pressure maintained in the first receptacle, thereby urging blood from within the first receptacle to the transfer bag.

8. An autologous blood transfusion system as defined in claim 7 wherein said canister further comprises an open face into which the blood transfer bag and first receptacle are compactly received, the open face being circumscribed by gasket means accommodating formation of a pressure seal at the juncture of the canister and the blood-receiving receptacle.

9. An autologous blood transfusion system as defined in claim 8 wherein said first receptacle comprises a depending skirt which, when connected to the canister, cooperates to define a receptacle for the transfer bag and wherein said pressure reducing means comprises a port mounted within said skirt.

10. An autologous transfusion system comprising in combination:
- a first rigid receptacle comprising means for receiving blood from a patient and means for imposing a negative pressure within the first receptacle to thereby urge blood from the receiving means into the first receptacle;
- a second rigid receptacle and a flexible liner situated within the second receptacle to receive blood from the first receptacle, means connecting the interior of the first receptacle with the interior of the flexible liner; and
- means for selectively changing the fluid pressure between the liner and the second receptacle in relation to the magnitude of negative pressure maintained in the first receptacle so as to selectively transfer blood in the first receptacle to the flexible liner.

11. An autologous transfusion system as defined in claim 10 further comprising means for communicating the blood within the second receptacle to a patient and means for increasing the fluid pressure between the second receptacle and the liner to urge blood from the liner into the patient.

12. An autologous transfusion system comprising in combination:
- a first receptacle comprising means for receiving blood from a patient, means for developing a negative pressure in the first receptacle so as to draw blood from the receiving means into the first receptacle;
- a second receptacle and a flexible blood-receiving bag normally situated within the second receptacle and selectively communicating with the interior of the first receptacle; and
- means for selectively decreasing fluid pressure between the flexible blood-receiving bag and the second receptacle below the negative pressure in the first receptacle so as to draw blood from the first receptacle into the flexible bag without interrupting the negative pressure in the first receptacle.

13. An autologous transfusion system as defined in claim 12 further comprising means for communicating blood out of the flexible bag and means for increasing the fluid pressure between the second receptacle and the flexible bag to expel blood from the bag.

14. A method of collecting blood from a patient and infusing the same blood back into the patient through a closed extracorporeal blood circuit comprising a blood aspiration device, a first receptacle, a second receptacle and a flexible liner within the second receptacle, the method comprising the steps of:
- creating suction within the blood aspiration device by developing a negative pressure in the first receptacle and selectively aspirating blood from the patient through the blood aspiration device;
- depositing the blood in the first receptacle;
- transferring the blood from the first to the second receptacle without interrupting the suction, said transfer being caused by reducing the fluid pressure between the second receptacle and the liner below the negative pressure in the first receptacle;
- thereafter increasing the fluid pressure between the liner and the second receptacle above the negative pressure maintained in the first receptacle so as to expel the blood in the second receptacle into the patient without interrupting the negative pressure in the first receptacle.

15. A method of infusing autologous blood into a patient through an extracorporeal blood circuit having a first receptacle and a second receptacle, the second receptacle having a flexible liner therein, the method comprising the steps of:
- creating a negative pressure within the first receptacle and selectively delivering blood from the patient into the first receptacle;
- overcoming the negative pressure in the first receptacle by decreasing the pressure between the second receptacle and the liner below the pressure in the first receptacle to thereby transfer the blood into the second receptacle from the first without interrupting the negative pressure in the first receptacle; and
- expelling the blood from the second receptacle by creating a positive fluid pressure between the liner and the second receptacle, said positive pressure being sufficiently greater than the negative pressure maintained in the first receptacle to permit expulsion of the blood from the second receptacle.

16. A method of infusing autologous blood into a patient as defined in claim 15 further comprising restricting the blood flow to unidirectional travel between the first and second receptacles.

17. A method of infusing autologous blood into a patient as defined in claim 15 further comprising connecting a transfer bag to the second receptacle and wherein said expelling step comprises transferring the blood collected in the second receptacle to the transfer bag, said transferring step being effected without interrupting the negative pressure in the first receptacle.

18. A method for collecting blood from a patient and infusing the same blood back into the patient, comprising the steps of:
- providing a closed extracorporeal blood circuit through which blood passes;
- creating suction within a blood-aspirating device and selectively aspirating blood from the patient through the blood-aspirating device;
- depositing the blood in a first receptacle;
- transferring the blood from the first receptacle to a flexible liner normally situated within a second receptacle by reducing the pressure between the liner and the second receptacle below the pressure in the first receptacle;
- separating the second receptacle from the first without interrupting the suction within the blood-aspirating device; and
- expelling blood from the second receptacle by exerting a positive fluid pressure with respect to the pressure in the first receptacle, said positive pressure being applied between the liner and the second receptacle.

19. In a method for autologous blood transfusion through an extracorporeal circuit comprising a first receptacle, a second receptacle and a flexible transfer bag removably connected to the first receptacle, the method comprising the steps of:
- reducing the pressure in the first receptacle and thereby aspirating blood therein;
- connecting a blood transfer bag to the first receptacle so as to provide unidirectional blood flow from the first receptacle to the transfer bag;

compactly placing the transfer bag into the second receptacle and forming a seal between the first and second receptacles;

reducing the pressure within the second receptacle below the reduced pressure in the first receptacle to thereby cause transfer of blood from the first receptacle to the transfer bag; and separating the transfer bag from the first receptacle for reinfusion into the patient.

20. In a method of autologous blood transfusion as defined in claim 19 wherein said separating step is preceded by removing the second receptacle from the first.

21. In a method of autologous blood transfusion as defined in claim 19 wherein said separating step is preceded by accessing the transfer bag through an opening in the second receptacle.

22. A method of collecting blood from a patient and infusing the same blood back into the patient through an extracorporeal blood circuit comprising a blood aspiration device, a first receptacle, a second receptacle and a flexible liner within the second receptacle, the method comprising the steps of:

creating suction within the blood aspiration device by developing a negative pressure in the first receptacle and selectively aspirating blood from the patient through the blood aspiration device;

depositing the blood in the first receptacle; and decreasing fluid pressure between the flexible liner and the second receptacle below the negative pressure maintained in the first receptacle to thereby draw blood from the first receptacle into the flexible liner.

* * * * *